(12) United States Patent　　　　(10) Patent No.: US 12,582,393 B2

Fleischer　　　　　　　　　　　　(45) Date of Patent: *Mar. 24, 2026

(54) RETRACTOR FOR SPINAL SURGERY

(71) Applicant: Gary Fleischer, Exeter, NH (US)

(72) Inventor: Gary Fleischer, Exeter, NH (US)

( * ) Notice: Subject to any disclaimer, the term of this patent is extended or adjusted under 35 U.S.C. 154(b) by 577 days.

This patent is subject to a terminal disclaimer.

(21) Appl. No.: 17/897,882

(22) Filed: Aug. 29, 2022

(65) Prior Publication Data

US 2022/0409196 A1　　Dec. 29, 2022

Related U.S. Application Data

(63) Continuation of application No. 16/595,071, filed on Oct. 7, 2019, now Pat. No. 11,457,908.

(60) Provisional application No. 62/741,793, filed on Oct. 5, 2018.

(51) Int. Cl.
| | |
|---|---|
| *A61B 17/02* | (2006.01) |
| *A61B 1/32* | (2006.01) |
| *A61B 17/00* | (2006.01) |

(52) U.S. Cl.
CPC ............ *A61B 17/0218* (2013.01); *A61B 1/32* (2013.01); *A61B 17/0206* (2013.01); *A61B 17/0293* (2013.01); *A61B 2017/00261* (2013.01)

(58) Field of Classification Search
CPC . A61B 17/0218; A61B 17/02; A61B 17/0293; A61B 1/32
See application file for complete search history.

(56) References Cited

U.S. PATENT DOCUMENTS

| | | | |
|---|---|---|---|
| 1,551,323 A | 8/1925 | Offerdahl | |
| 4,012,155 A | 3/1977 | Morris | |
| 4,573,448 A | 3/1986 | Kambin | |
| RE33,258 E | 7/1990 | Onik et al. | |
| 5,015,255 A | 5/1991 | Kuslich | |
| 5,269,305 A * | 12/1993 | Corol ..................... A61B 90/11 |
| | | | 378/20 |
| 5,313,962 A | 5/1994 | Obenchain | |
| 5,383,884 A | 1/1995 | Summers | |
| 5,700,291 A | 12/1997 | Kuslich et al. | |
| 5,702,454 A | 12/1997 | Baumgartner | |
| 5,762,629 A | 6/1998 | Kambin | |
| 5,976,146 A | 11/1999 | Ogawa et al. | |
| 6,095,149 A | 8/2000 | Sharkey et al. | |
| 6,127,597 A | 10/2000 | Beyar et al. | |
| 6,139,493 A * | 10/2000 | Koros ................ A61B 17/0206 |
| | | | 600/231 |
| 8,568,306 B2 | 10/2013 | Hardenbrook | |
| 8,795,167 B2 | 8/2014 | Ainsworth et al. | |
| 9,867,605 B2 | 1/2018 | Adams | |

(Continued)

FOREIGN PATENT DOCUMENTS

WO　　　　9947055 A1　　9/1999

*Primary Examiner* — Ellen C Hammond

(74) *Attorney, Agent, or Firm* — Hall Estill Law Firm

(57) ABSTRACT

A retractor assembly and minimally invasive surgical techniques and implants. Such embodiments include techniques and implants for provision of therapy to a spine from a lateral approach. Embodiments of the invention include minimally invasive surgical techniques using one or more extended retractors to create an extended access route such as the non-limiting example of lateral access to the spine.

8 Claims, 10 Drawing Sheets

(56) References Cited

U.S. PATENT DOCUMENTS

2010/0286486 A1* 11/2010 Parker ................ A61B 17/1757
                                                    600/235
2017/0333023 A1* 11/2017 Adams ............... A61B 17/0293

* cited by examiner

32

RETRACTOR FOR SPINAL SURGERY

CROSS REFERENCE TO RELATED APPLICATIONS

This application is a continuation application of U.S. Patent Application having Ser. No. 16/595,071, filed Oct. 7, 2019, which is a conversion application of U.S. Provisional Patent Application 62/741,793, filed on Oct. 5, 2018, which are hereby incorporated by reference.

FIELD OF THE INVENTION

This disclosure relates generally to minimally invasive surgical techniques including techniques and implants for provision of therapy to a spine from a lateral approach. Implants that may be used with other approaches to the spine are disclosed. Minimally invasive surgical techniques using one or more extended retractors to create an extended access route such as the non-limiting example of lateral access to the spine are disclosed.

BACKGROUND OF THE INVENTION

It has been estimated that 70% of adults have had a significant episode of back pain or chronic back pain emanating from a region of the spinal column or backbone. Many people suffering chronic back pain or an injury requiring immediate intervention resort to surgical intervention to alleviate their pain.

The spinal column or backbone encloses the spinal cord and consists of 33 vertebrae superimposed upon one another in a series which provides a flexible supporting column for the trunk and head. The vertebrae cephalad (i.e., toward the head or superior) to the sacral vertebrae are separated by fibrocartilaginous intervertebral discs and are united by articular capsules and by ligaments. The uppermost seven vertebrae are referred to as the cervical vertebrae, and the next lower twelve vertebrae are referred to as the thoracic, or dorsal, vertebrae. The next lower succeeding five vertebrae below the thoracic vertebrae are referred to as the lumbar vertebrae and are designated L1-L5 in descending order. The next lower succeeding five vertebrae below the lumbar vertebrae are referred to as the sacral vertebrae and are numbered S1-S5 in descending order. The final four vertebrae below the sacral vertebrae are referred to as the coccygeal vertebrae. In adults, the five sacral vertebrae fuse to form a single bone referred to as the sacrum, and the four rudimentary coccyx vertebrae fuse to form another bone called the coccyx or commonly the "tail bone". The number of vertebrae is sometimes increased by an additional vertebra in one region, and sometimes one may be absent in another region.

Typical lumbar, thoracic and cervical vertebrae consist of a ventral or vertebral body and a dorsal or neural arch. In the thoracic region, the ventral body bears two costal pits for reception of the head of a rib on each side. The arch which encloses the vertebral foramen is formed of two pedicles and two lamina. A pedicle is the bony process which projects backward or posteriorly from the body of a vertebra connecting with the lamina on each side. The pedicle forms the root of the vertebral arch. The vertebral arch bears seven processes: a dorsal spinous process, two lateral transverse processes, and four articular processes (two superior and two inferior). A deep concavity, inferior vertebral notch, on the inferior border of the arch provides a passageway or spinal canal for the delicate spinal cord and nerves. The successive vertebral foramina surround the spinal cord. Articulating processes of the vertebrae extend posteriorly of the spinal canal.

The bodies of successive lumbar, thoracic and cervical vertebrae articulate with one another and are separated by the intervertebral spinal discs. Each spinal disc comprises a fibrous cartilage shell enclosing a central mass, the "nucleus pulposus" (or "nucleus" herein) that provides for cushioning and dampening of compressive forces to the spinal column. The shell enclosing the nucleus comprises cartilaginous endplates adhered to the opposed cortical bone endplates of the cephalad and caudal vertebral bodies and the "annulus fibrosis" (or "annulus" herein) comprising an annular fibrosis layer of collagen fibers running circumferentially around the nucleus pulposus and connecting the cartilaginous endplates. The nucleus contains hydrophilic (water attracting) micropolysacharides and fibrous strands. The nucleus is relatively inelastic, but the annulus can bulge outward slightly to accommodate loads axially applied to the spinal motion segment.

The intervertebral discs are anterior to the spinal canal and located between the opposed end faces or endplates of a cephalad and a caudal vertebral body. The inferior articular processes articulate with the superior articular processes of the next succeeding vertebra in the caudal (i.e., toward the feet or inferior) direction. Several ligaments (supraspinous, interspinous, anterior and posterior longitudinal, and the ligamenta flava) hold the vertebrae in position yet permit a limited degree of movement. The assembly of two vertebral bodies, the interposed, intervertebral, spinal disc and the attached ligaments, muscles and facet joints is referred to as a "spinal motion segment".

The relatively large vertebral bodies located in the anterior portion of the spine and the intervertebral discs provide the majority of the weight bearing support of the vertebral column. Each vertebral body has relatively strong, cortical bone layer comprising the exposed outside surface of the body, including the endplates, and weak, cancellous bone comprising the center of the vertebral body.

A number of spinal disorders are caused by traumatic spinal injuries, disease processes, aging processes, and congenital abnormalities that cause pain, reduce the flexibility of the spine, decrease the load bearing capability of the spine, shorten the length of the spine, and/or distort the normal curvature of the spine. These spinal disorders and various treatments that have been clinically used or proposed are first described as follows.

With aging, the nucleus becomes less fluid and more viscous and sometimes even dehydrates and contracts (sometimes referred to as "isolated disc resorption") causing severe pain in many instances. In addition, the annulus tends to thicken, desiccate, and become more rigid, lessening its ability to elastically deform under load and making it susceptible to fracturing or fissuring.

One form of degeneration of the disc occurs when the annulus fissures or is rent. The fissure may or may not be accompanied by extrusion of nucleus material into and beyond the annulus. The fissure itself may be the sole morphological change, above and beyond generalized degenerative changes in the connective tissue of the disc, and disc fissures can nevertheless be painful and debilitating. Biochemicals contained within the nucleus are alleged to escape through the fissure and irritate nearby structures.

A fissure also may be associated with a herniation or rupture of the annulus causing the nucleus to bulge outward or extrude out through the fissure and impinge upon the spinal column or nerves (a "ruptured" or "slipped" disc).

With a contained disc herniation, the nucleus may work its way partly through the annulus but is still contained within the annulus or beneath the posterior longitudinal ligament, and there are no free nucleus fragments in the spinal canal. Nevertheless, even a contained disc herniation is problematic because the outward protrusion can press on the spinal cord or on spinal nerves causing sciatica.

Another disc problem occurs when the disc bulges outward circumferentially in all directions and not just in one location. This occurs when over time, the disc weakens, bulges outward and takes on a "roll" shape. Mechanical stiffness of the joint is reduced and the spinal motion segment may become unstable shortening the spinal cord segment. As the disc "roll" extends beyond the normal circumference, the disc height may be compromised, and foramina with nerve roots are compressed causing pain. In addition, osteophytes may form on the outer surface of the disc roll and further encroach on the spinal canal and foramina through which nerves pass. The cephalad vertebra may eventually settle on top of the caudal vertebra. This condition is called "lumbar spondylosis".

In addition, various types of spinal column displacement disorders are known in one or more spinal motion segment that are hereditary or are caused by degenerative disease processes or trauma. Such spinal displacement disorders include scoliosis (abnormal lateral curvature of the spine), kyphosis (abnormal forward curvature of the spine, usually in the thoracic spine), excess lordosis (abnormal backward curvature of the spine, usually in the lumbar spine), spondylolisthesis (forward displacement of one vertebra over another, usually in the lumbar or cervical spine). At times the displacement disorder is accompanied by or caused by a fracture or partial collapse of one or more vertebrae or degeneration of a disc. Patients who suffer from such conditions can experience moderate to severe distortion of the axial skeletal structure, diminished ability to bear loads, loss of mobility, extreme and debilitating pain, and oftentimes suffer neurologic deficit in nerve function.

The vast majority spinal surgery involves the lower lumbar vertebrae designated as the fourth lumbar vertebra ("L4"), the fifth lumbar vertebra ("L5"), and the first sacral vertebra ("SI"). Persistent low back pain is attributed primarily to degeneration of the disc connecting L5 and SI. Traditional, conservative methods of treatment include bed rest, pain and muscle relaxant medication, physical therapy or steroid injection. Upon failure of conservative therapy spinal pain (assumed to be due to instability) has traditionally been treated by spinal fusion, with or without instrumentation, which causes the vertebrae above and below the disc to grow solidly together and form a single, solid piece of bone.

Highly invasive, open surgical procedures have been developed and used to perform a "complete discectomy" to surgically remove the disc, and the vertebral bodies are then fused together. The removal of the disc involves removing the nucleus, cutting away the cartilaginous endplates adhered to the opposed cortical bone endplates of the cephalad and caudal vertebral bodies, and removing at least a portion of the annulus. Fusion of the vertebral bodies involves preparation of the exposed endplate surfaces by decortication (scraping the endplate cortical bone) and the deposition of additional bone into disc space between the prepared endplate surfaces. The complete discectomy and fusion may be performed through a posterior surgical route (from the back side of the patient) or an anterior surgical route (from the front side of the patient). The removed vertebral bone may be just the hard cortical bone or may include soft cancellous soft bone in the interior of the vertebral bodies. Controversy exists regarding the preferred method of performing these fusions for various conditions of the spine. Sometimes, non-biological materials are used to augment and support the bone graft and/or fixation systems.

Sometimes, the fixation is performed from the posterior route (posterior fixation), or from the anterior route (anterior fixation), or even both sides (anterior-posterior fixations or circumferential fusion).

Current treatment methods other than spinal fusion for symptomatic disc rolls and herniated discs include "laminectomy" which involves the posterior surgical exposure of the annulus and surgical excision of the symptomatic portion of the herniated disc followed by a relatively lengthy recuperation period.

Various other surgical treatments that attempt to preserve the intervertebral spinal disc and to simply relieve pain include a "nucleotomy" or "disc decompression" to remove some or most of the interior nucleus thereby decompressing and decreasing outward pressure on the annulus. In less invasive microsurgical procedures known as "microlumbar discectomy" and "automated percutaneous lumbar discectomy", the nucleus is removed by suction through a needle laterally extended through the annulus. Although these procedures are less invasive than open surgery, they nevertheless suffer the possibility of injury to the nerve root and dural sac, perineural scar formation, reherniation of the site of the surgery, and instability due to excess bone removal. Moreover, they involve the perforation of the annulus.

Although damaged discs and vertebral bodies can be identified with sophisticated diagnostic imaging, the surgical procedures are so extensive that clinical outcomes are not consistently satisfactory. Furthermore, patients undergoing such fusion surgery experience significant complications and uncomfortable, prolonged convalescence. Surgical complications include disc space infection, nerve root injury, hematoma formation, and instability of adjacent vertebrae.

Many surgical techniques, instruments and spinal disc implants have been described in the medical literature and in patents that are directed to providing less invasive, percutaneous, lateral access to a degenerated intervertebral spinal disc. Then, instruments are introduced through lateral disc openings made through the annulus for performing a discectomy and implanting bone growth materials or biomaterials or spinal disc implants inside the annulus. Or, one or more laterally extending space or hole is bored through the disc to receive one or more laterally inserted spinal disc implant or bone growth material to promote fusion or to receive a pre-formed, artificial, functional disc replacement implant as typified by U.S. Pat. No. 5,700,291.

Percutaneous lateral procedures and instruments for performing such discectomies are disclosed in U.S. Pat. Nos. Re33,258, 4,573,448, 5,015,255, 5,313,962, 5,383,884, 5,702,454, 5,762,629, 5,976,146, 6,095,149, and 6,127,597 and in PCX publication WO 99/47055, for example. A laparoscopic technique and apparatus for traversing the retroperitoneal space from an abdominal skin incision to an anterior surface of the disc annulus and performing a discoscopy is disclosed in the '962 patent, for example. Percutaneous surgical disc procedures and apparatus that accesses the disc in a posterolateral approach from a skin incision in the patient's back are described in the '629 and '448 patents, for example.

The nucleus is fragmented by various mechanical cutting heads as disclosed, for example in the '258, '962, '884, and '597 patents, for example. Or, thermal or laser energy is applied to desiccate the nucleus and to stiffen the annulus as described in the '149 patent, for example. Or, the nucleus and portions of the cephalad and caudal vertebral bodies are mechanically cut away to enlarge the disc space as described in the PCX '055 publication and in the '255 patent, for example. Irrigation fluid is introduced into the disc space or cavity and the fragments or desiccation by-products of the nucleus and any bone and annulus fragments are aspirated from the disc space or cavity. The irrigation and aspiration is effected through an access cannula positioned against the opening through the annulus of the herniated disc as disclosed in the '629 patent, for example, or through a lumen of the discectomy instrument, as disclosed in the '258 patent, for example. A measure of safety and accuracy is added to these operative procedures by the artiroscopic visualization of the annulus and other important structures which lie in the path of the instruments, such as the spinal nerve.

The above-described procedures involve invasive surgery that laterally exposes the anterior or posterior (or both) portions of the vertebrae and intervertebral spinal disc. Extensive muscular stripping and bone preparation can be necessary. As a result, the spinal column can be further weakened and/or result in surgery induced pain syndromes. Thus, presently used or proposed surgical fixation and fusion techniques involving the lower lumbar vertebrae suffer from numerous disadvantages.

Methods and apparatus for accessing the discs and vertebrae by lateral surgical approaches that purportedly reduce muscular stripping (and that are similar to those disclosed in the above-referenced '629 and '888 patents) are described in U.S. Pat. No. 5,976,146. The intervening muscle groups or other tissues are spread apart by a cavity forming and securing tool set disclosed in the '146 patent to enable endoscope aided, lateral access to damaged vertebrae and discs and to perform corrective surgical procedures. However, a challenge remains with the lateral exposure in association with the instrumentation utilized to accomplish such lateral exposure.

A specific type of apparatus utilized for tubular lateral disclosure is described in U.S. Pat. No. 8,795,167 (the '167 patent), which is incorporated by reference in its entirety. Such technology allows for the utilization of minimally invasive techniques using internal retractors that may be reversibly expanded with a removable retractor inserter by utilizing a linkage jack to create an extended access route. An advantage associated with the technology disclosed in the '167 patent is that it enables so-called "shallow docking." Such "shallow docking" allows for a surgeon to dissect the psoas muscle under direct visualization as opposed to only with the assistance of neuro-monitoring to, for instance, avoid nerve damage or any other tissues in the space, such as bowel. In this and similar technologies, often referred to "tube within a tube" technologies, a common mode of functionality is that a second tube pushed into a first pushes the exterior surface (typically comprising blades) radially. However, a problem associated with such technologies is that in such configuration, the blades would need to move simultaneously. Typically, the blades are arranged in a two-bladed configuration, which is associated with the challenge of precision. Moreover, unsolved efficiency problems remain associated with the need to initially place both blades in a two-bladed configuration simultaneously during surgery. In the two-bladed configuration, for instance, the blades depend on one another to accomplish fixation. It is required that one or more users insert and hold two blades at once to dock the retractor, and then to subsequently unlock the mechanism, all blades must be dislodged together. Therefore, a still remaining challenge is that during surgery, at least three hands are required simultaneously (requiring more than one user) to utilize the "tube within a tube" technology—one hand holds each of two blades, and another hand holds a locking mechanism. Relatedly, if only one blade were in place, the tolerances would not hold, requiring another person to hold the blade or another part of the related apparatus. The resultant still unsolved challenge with this type of technology is the added complexity of incorporating another person other than the surgeon into a procedure during surgery can have catastrophic consequences in the worst case, resulting in irreversible harm to a patent with an open exposure by contact in an unintended manner with someone other than a trained surgeon.

A related problem associated with the technologies related to the device for tubular lateral exposure, and other similar devices that incorporate manual retraction blades, is that multiple people are required to hold the device in place during surgery. Due to the configuration of such devices, at least three hands are required to hold and configure retraction devices and their multiple blades at various points in time during surgery. Therefore, a surgeon operating alone cannot utilize and precisely position and operate the device without the assistance of another person.

Another problem still facing many retraction apparatuses known in the prior art is that fixing components of the retraction apparatuses creates many undesirable forces relative to the components and the body.

Another problem still facing many retraction apparatuses known in the prior art is that in the most common implementation, the approach to the disk requires precise alignment with the disk space perpendicular to the long axis of the spine. This may necessitate multiple incisions for multiple disk levels. It also often creates difficulty approaching the L4-5 disk space perpendicular to the spine, as the iliac crest or pelvic brim may overlie the disk space necessitating the ability to approach the level at an angle.

There remains a need for methods and apparatus for performing therapeutic procedures in the spine in an improved minimally invasive, low trauma, manner.

BRIEF DESCRIPTION OF FIGURES

FIG. 1013 depicts a view of a four-bladed retractor in an embodiment of the invention as assembled.

DETAILED DESCRIPTION

Figure 1:
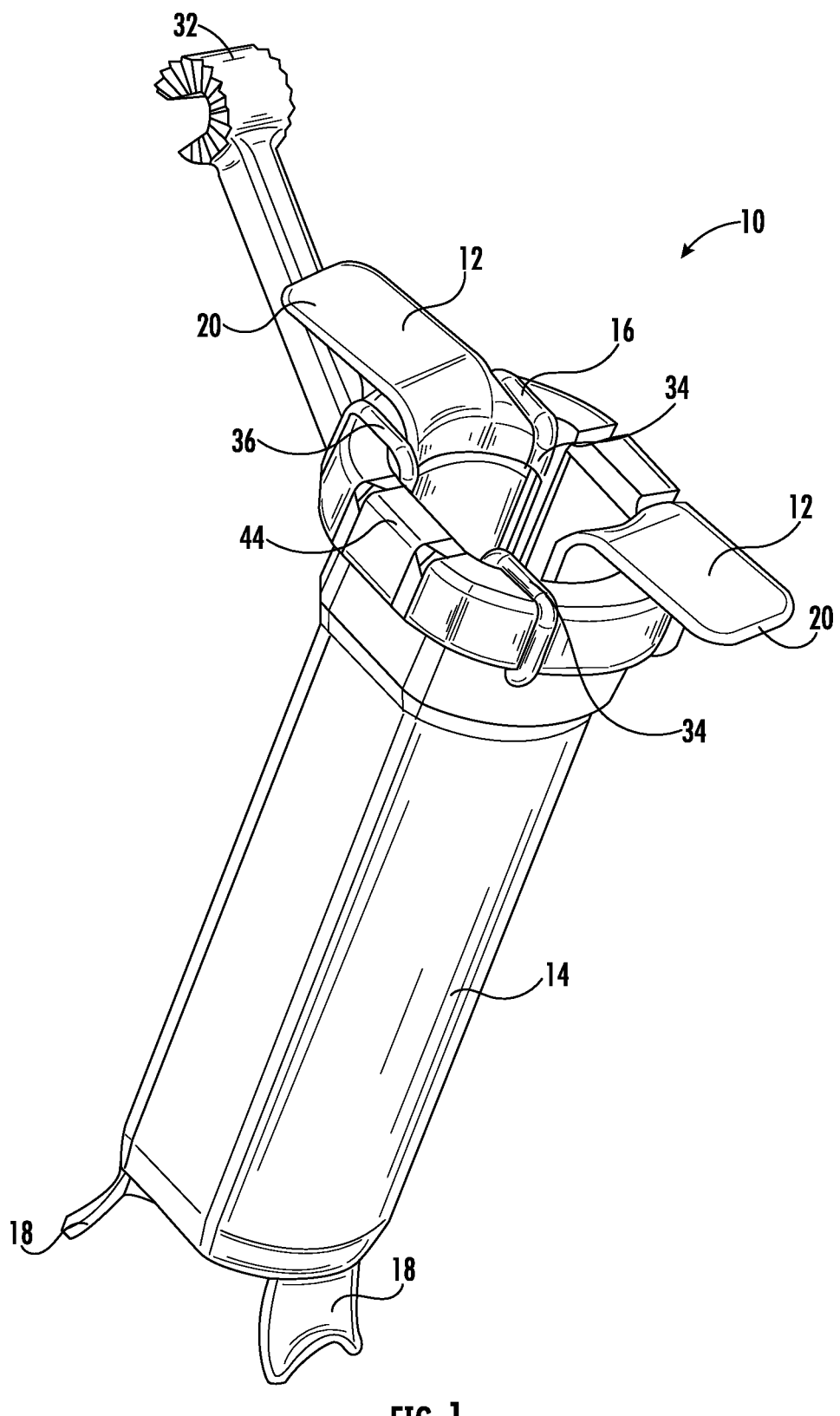
FIG. 1 depicts a perspective view of an assembly of the preferred embodiment of the invention.

In the context of the present disclosure, as used herein the term "assembly" refers to implants, instruments and instrument systems which are configured to comprise multiple components, which may or may not be contiguous. It is further understood that individual components may themselves be configured as sub-assemblies, e.g., comprising a plurality of component materials, and that the formation of the components may involve intermediate processes or appliances. The present inventive subject matter relates to concepts described in U.S. Pat. Nos. 8,795,167 and 8,568, 306, both of which are incorporated by reference herein.

It will also be understood that upon formation of assemblies from multiple components and deployment, individual components of the present disclosure may or may not remain as discernibly distinct. It will also be understood that, for convenience, system components may be packaged and provided either individually, or as in "kits," and either as reusable or disposable.

As used herein, the term "biocompatible" refers to an absence of chronic inflammation response or cytotoxicity when or if physiological tissues are in contact with, or exposed to (e.g., wear debris) the materials and devices of the present disclosure. In addition to biocompatibility, in another aspect of the present disclosure it is preferred that the materials comprising the instrument systems are sterilizable.

In one aspect of the present disclosure, certain components of the device assemblies and systems of the present disclosure are configured to comprise biocompatible materials and are able to withstand, without wear, multiple cycles/procedures without failing. It will be further understood that the length and dimensions of instruments and components described herein will depend in part on the target site selection of the treatment procedure and the physical characteristics of the patient, as well as the construction materials and intended functionality, as will be apparent to those of skill in the art.

In order to make it easier for a reader to find certain sections of this document that are of particular interest to the reader, a series of headings have been used. These headings are solely for the purpose of helping readers navigate the document and do not serve to limit the relevance of any particular section to exclusively the topic listed in the heading.

In the context of this discussion: anterior refers to in front of the spinal column; (ventral) and posterior refers to behind the column (dorsal); cephalad means towards the patient's head (sometimes "superior"); caudal (sometimes "inferior") refers to the direction or location that is closer to the feet. Proximal is closer to the beginning of the channel and thus the surgeon; distal is further from the beginning of the channel and in use more distant from the surgeon. When referencing tools including cutters or other tools distal would be the end intended for insertion into the access channel and proximal refers to the other end, generally the end closer to the handle for the tool.

The sequence of operations (or steps) is not limited to the order presented in the claims or figures unless specifically indicated otherwise.

The present application has a range of teachings that may be used to advantage in a number of settings. However, to provide these teachings with clarity, it is useful to describe one use of many of the teachings in great detail. The use described below is to access a lateral portion of a human spine using a lateral approach in order to provide therapy such as a fusion procedure to a vertebral motion segment. This process may be broken down to a natural sequence of:

Positioning the patient in accordance with techniques known by one skilled in the art;

Creating an access channel to the psoas muscle;

Creating an opening through the psoas muscle;

Enlarging an access channel through the psoas muscle;

Preparing the disc space;

Delivering an implant which may include fusion promoting materials; and

Closing the access path;

Psoas Muscle.

The psoas muscle is a major muscle in the human body used to stabilize the base of the spine. The psoas muscle is involved in hip flexion and rotation. The psoas muscle runs on both lateral sides of the lumbar spine. The psoas muscle is of interest for spine surgery in that this tough muscle must be traversed to access lumbar discs from a lateral approach. Positioning the Patient.

Those of skill in the art are familiar with various techniques for positioning a patient to facilitate access to a spinal disc space from a lateral approach. This knowledge includes making adjustments as needed to provide access around the iliac crest for lateral access to the lumbo-sacral spine. Thus, this description will be brief and should be considered exemplary rather than limiting to the teachings of the present disclosure.

A patient may be positioned in a lateral decubitus position on a radiolucent breaking table. The patient may be stabilized and secured to the table with surgical tape:

A) just below the iliac crest;

B) over the thoracic region;

C) from the iliac crest to the knee, then secured to the table; and

D) from the table to the knee, past the ankle, then secured back to the table.

Placing the table break at the iliac crest may work well when targeting the L3/L4 or L4/L5 disc spaces. When targeting the L1/L2 or the L2/L3 disc spaces it may be helpful to position the patient so that the table break is cephalad of the iliac crest. After positioning, a true Anterior/ Posterior (A/P) image may be obtained of the targeted disc using a C-arm imaging device (not shown). Likewise, a true lateral image may be obtained using the C-arm imaging device. A line in the anterior/posterior direction may be drawn on the patient to represent the midline of the targeted disc. Additional lines may be added to represent the front, back, and midline of the disc space in the lateral direction.

After conventional draping and preparation of the surgical site, at table mounted retractor arm (not shown) may be mounted to the table for use later in the process. Access to Psoas.

In an embodiment, to access the psoas, the surgeon makes an anterior-to-posterior incision over the center marking of the disc space. This incision may be 35 to 40 millimeters in length for some patients. The incision may be transverse, vertical, or oblique depending on preference.

Using finger or blunt dissection, the surgeon opens the incision down to fascia over the external oblique muscles. Incise fascia in line with the muscle fibers. Continue blunt or finger dissection through the muscle layers into the retroperitoneal space to the psoas muscle. After blunt or finger dissection has made a pathway to the psoas muscle, the access channel may be enlarged through conventional means such as a sequence of dilation tubes of increasing diameter and decreasing length. The term enlarge is meant to include the various processes known in the art to increase the volume of an opening. This would include dilation, dissection, retraction, or combinations thereof, and analogous actions.

Depth indications on the outermost dilator may be used to select a channel retractor, which may comprise a four-bladed retractor as depicted in FIGS. 10A-10E. For example the first outermost dilator has depth markings for 100 millimeters, 120 millimeters and 140 millimeters on one side along the longitudinal shaft of the outermost dilator. The surgeon notes the value of the marker closest to the patient's skin and selects a corresponding channel retractor (discussed below) to insert over the outer surface of the outermost dilator. The channel retractor is advanced distally down to the psoas muscle and then secured with the table mounted retractor arm with a stabilization arm. All of the tissue dilators are removed and a lateral fluoroscopic image is obtained to confirm placement of the channel retractor is centered over the targeted disc space or appropriately aligned to access it at a desired angle. If the channel retractor is not centered, adjustments are made so that the channel retractor is positioned directly over the targeted disc or appropriately aligned to access it at a desired angle.

FIGS. 10A-10E shows an example of a four-bladed retractor. Note that the four-bladed retractor may have a substantially uniform cross section (as taken with respect to the longitudinal axis). The cross section of the four-bladed retractor may be round (uniform radius), elliptical, square, oblong, or other shapes. In many instances the cross section will have rounded surfaces even for shapes such as a square or rectangle that is longer than it is wide. The cross section of the four-bladed retractor in FIGS. 10A-10E may be described as a rounded rectangle as it has a pair of curved ends separated by straight walls. The four-bladed retractor is sometimes called a tubular retractor as it comprises a lumen that is an opening at a proximal end extending throughout its length to an opening at a distal end, the four-bladed retractor thus having an inner perimeter. The four-bladed retractor may have a stabilizer arm for use to connect to a table mounted retractor arm.

Creating an Opening in the Psoas Muscle.

To prepare for work on the psoas muscle, it may be useful to add lighting. One way to add lighting is to plug one end of a fiber optic cable into a light source in accordance with manufacturer's instructions. The other end of the fiber optic cable may be attached to a stadium mount light.

As nerves are in the psoas muscle and care is taken to avoid damaging the nerves, those of skill in the art understand the process of neuromonitoring to locate the positioning of the nerves. As neuromonitoring is not the focus of the present application, details on the process of neuromonitoring are not included here.

The top surface of the psoas muscle is split between the muscle fibers typically using a Penfield dissector or a Cobb dissector. Some surgeons may prefer a straight dissector, and some may prefer an angled dissector After the psoas muscle is split, some surgeons will choose to insert a 90 degree nerve retractor down the side of the dissector used to maintain the split in the psoas muscle.

A guide pin (not shown) may be inserted along the nerve retractor (or dissector) through the split in the psoas muscle into the interior of the targeted disc space. The distal end of the guide pin may be inserted five to ten millimeters into the disc space. Once the guide pin is positioned, the nerve retractor may be removed from the incision.

A lateral fluoroscopy image may be taken to confirm that the guide pin is in the anterior/posterior center of the disc space. If the guide pin is properly positioned, an anterior/posterior fluoroscopic view may be used to confirm that the channel retractor is centered over the guide pin. Once the channel retractor position has been adjusted to be centered over the centered guide pin, the guide pin may be removed.

While it is thought that work on the psoas muscle is best done after the channel retractor is placed over the series of dilators, one of skill in the art will recognize that work to create the initial opening in the psoas muscle could happen before placing the channel retractor such as through use of tools that are inserted through the outermost dilator (after one, some or all of the inner dilators are removed).

Creating an Access Channel in the Psoas Muscle.

Enlarging the small opening created by the initial opening in the tough fibrous psoas muscle is challenging, even after the channel retractor is properly aligned and provides a working channel from outside the patient to the edge of the psoas muscle. However, sufficient force needs to be applied to expand the psoas muscle and then the enlarged opening in the psoas muscle should be maintained as a working channel to the disc space to allow for the surgical procedure on the disc, such as a fusion procedure. The channel retractor or other channel retractors as shown throughout may be constructed of a material that is substantially transparent to fluoroscopy. The channel retractor may have a series of one or more markers that are radio-opaque or at least substantially more radio-opaque than the channel retractor. The more opaque markers show clearly on fluoroscopy imaging to help discern the placement and alignment of the channel retractor relative to various component including landmarks in the patient's body and other radio-opaque tools or components. Markers are frequently spheres or rods but other shapes could be used. Tantalum is an example of a material used for markers.

Figure 3:
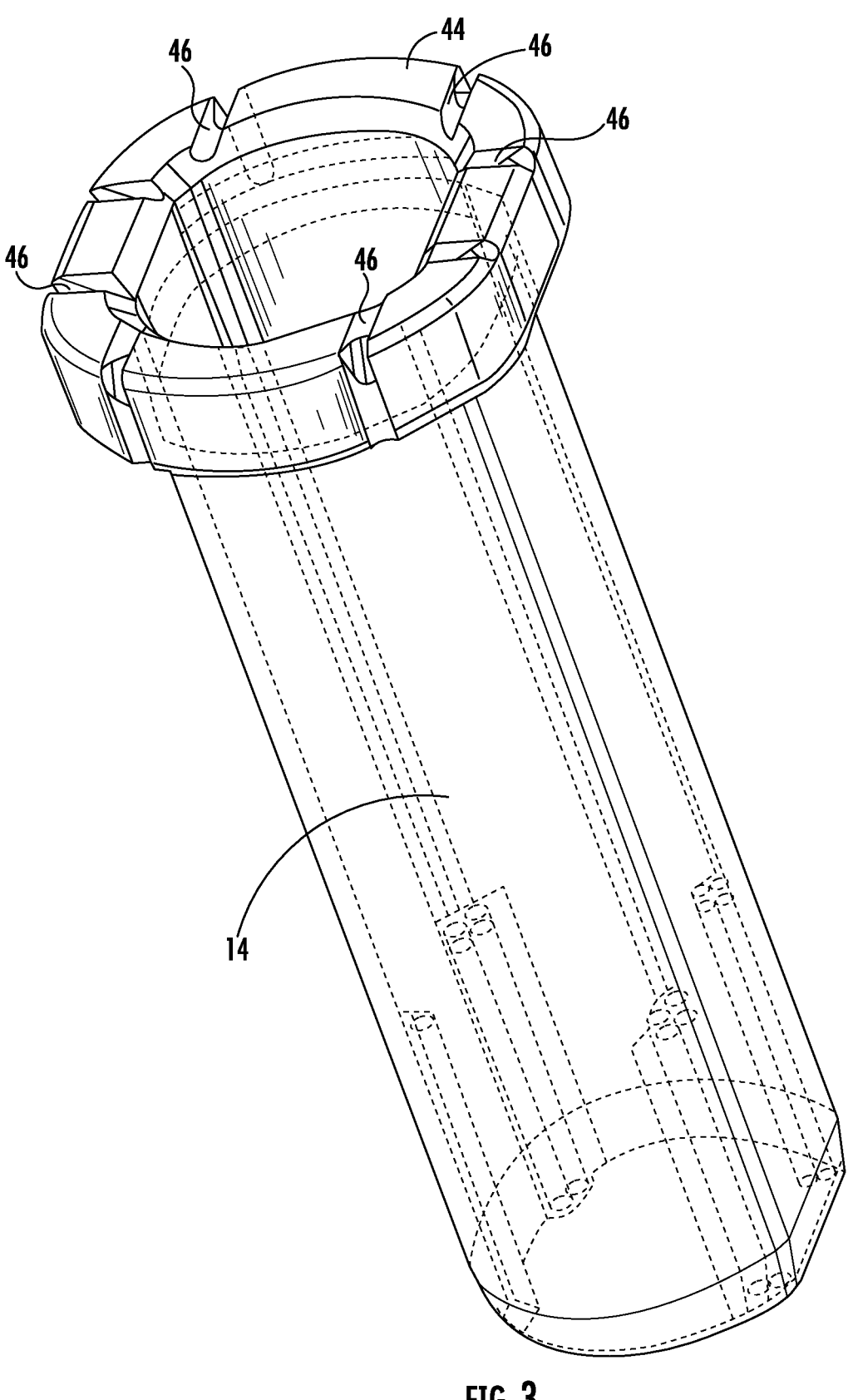
FIG. 3 depicts the main body of the tubular retractor in an embodiment of the invention.
Figure 4:
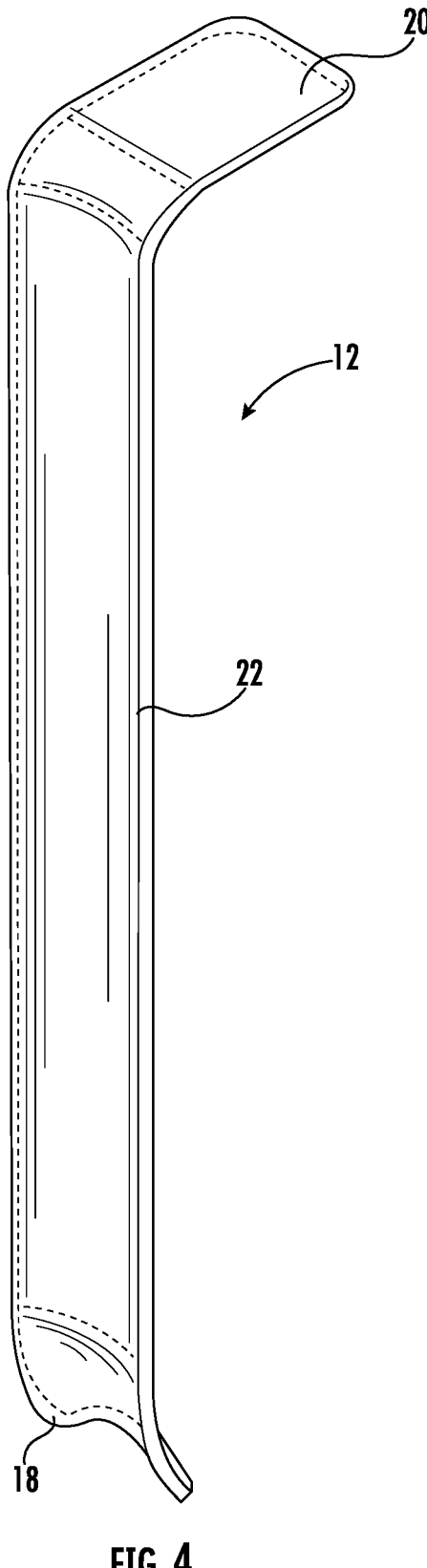
FIG. 4 depicts a single manual retractor blade in an embodiment of the invention.

Referring now to FIG. 1, shown therein is a retractor assembly 10 that incorporates a plurality of retractor blades 12 used to move and position tissue in a desired area, a channel retractor 14 for permitting access to the surgical site, and a spring clip 16 for securing the retractor blades 12 in position relative to the channel retractor 14, shown in more detail in FIG. 3. A retractor blade 12 as contemplated herein is depicted in FIG. 4. In one embodiment, the one or more retractor blades 12 are configured such that at least one of the plurality of retractor blades 12 can be manipulated independently from the other blades 12. In such embodiment, the independent manipulation of one of the plurality of retractor blades 12 allows for customized access to the surgical site. Each of the retractor blades 12 has a tissue end 18 for engaging the tissue around the surgical site to maintain access to the surgical site, a handle end 20 for providing a user the ability to easy grab and manipulate each retractor blade 12, and body 22 that extends through the channel retractor 14.

Each of the retractor blades 12 in an embodiment comprises medical grade stainless steel, which the present inventor has recognized demonstrates the characteristics of sufficient stiffness to provide a relatively thin wall, while enabling the transfer of adequate force to enlarge a gap in the psoas muscle. However, medical grade stainless steel is radio opaque and will make lateral visualization difficult for items in the channel retractor 14. In an alternative embodiment, each of the retractor blades 12 comprises aluminum. The present inventor has recognized that aluminum demonstrates the characteristics of radio-translucency, but would require thicker walls to provide the same strength as stainless steel, if necessary. The aluminum inner sleeves may be made with Tantalum markers so that the placement of the inner sleeve may be indicated in fluoroscopic images. In an alternative embodiment, the one or more retractor blades 12 comprise aluminum and stainless steel in varying configurations.

Figure 7:
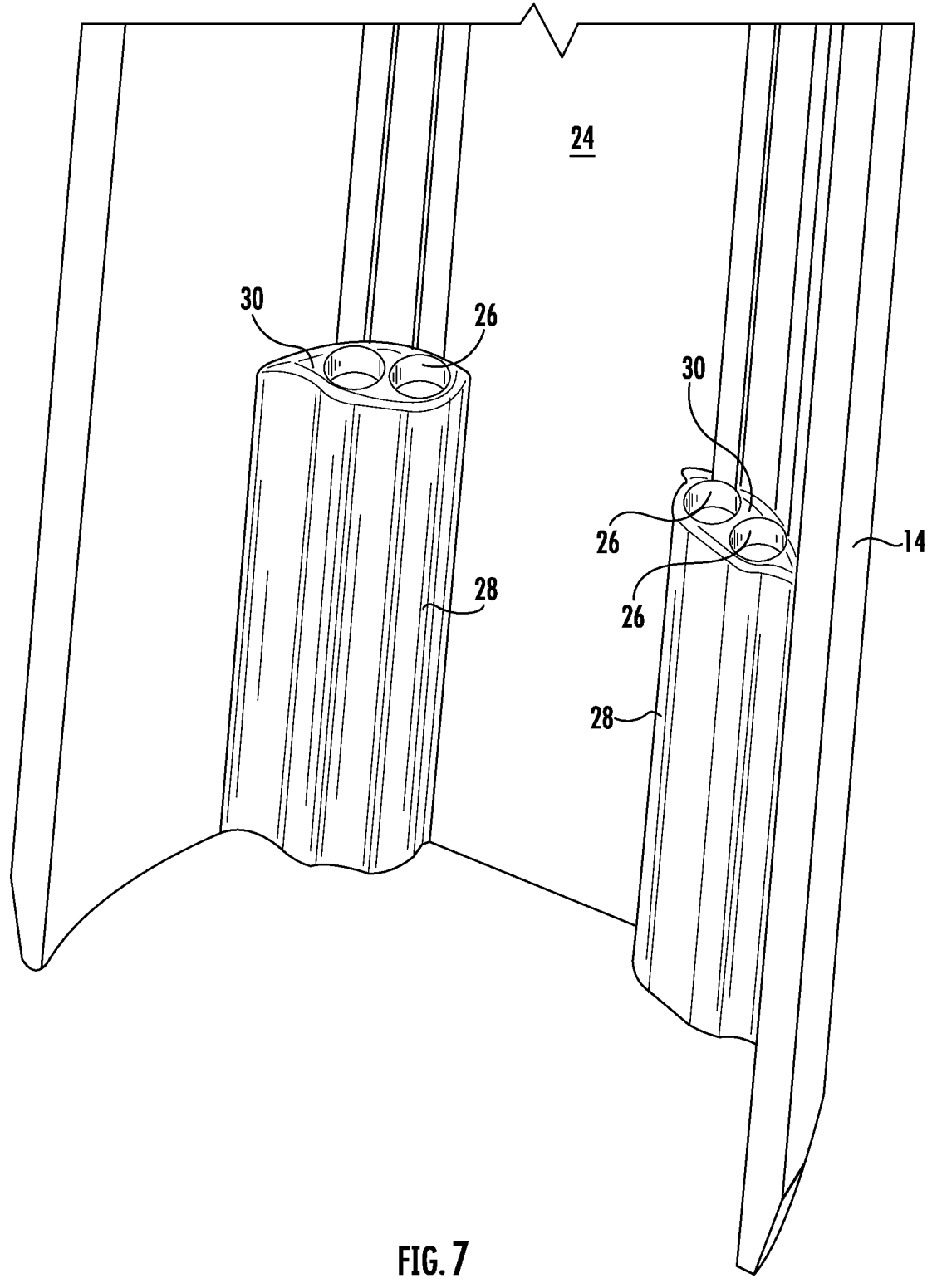
FIG. 7 depicts clip attachment holes integrated into the main body of the tubular retractor as configured in an embodiment of the invention.

In use of the retractor assembly 10, each of the individual retractor blades 12 are inserted into the psoas muscle. Following insertion, each of the retractor blades 12 is individually pulled, by the surgeon, in a substantially radial direction to an inner wall 24 of the channel retractor 14. A spring clip 16 can then be inserted. In one embodiment, the spring clip 16 is placed through the ralingue feature. In an alternative embodiment, the spring clip 16 is placed through one or more distal holes 26 disposed in the channel retractor 14, as depicted in FIG. 7, to provide distal fixation of the spring clip 16 and one or more retractor blades 12. In one embodiment, the channel retractor 14 includes protruded portions 28 where the distal holes 26 are disposed in a top portion 30 of the protruded portions. The individual placement of each of the retractor blades 12 associated with embodiments of the invention can be repeated by one surgeon for each of the one or more retractor blades 12 as needed.

The present disclosure sets forth an improved solution for extending the working channel beyond the channel retractor 14 and through a dense tissue such as the psoas muscle.

An embodiment of the invention comprises a retractor 14 with four blades, as depicted in FIGS. 10A-10E. In such embodiment, the four-bladed retractor may be used to mitigate anatomies that promoted tissue creep. The present inventor has recognized that due to anatomical differences, the utilization of retractors with only two or three blades can be less than ideal, as the tissue moves around the blades during or after retraction. In a four-bladed embodiment, the invention mitigates the tissue creep problem more advantageously.

Figure 2:
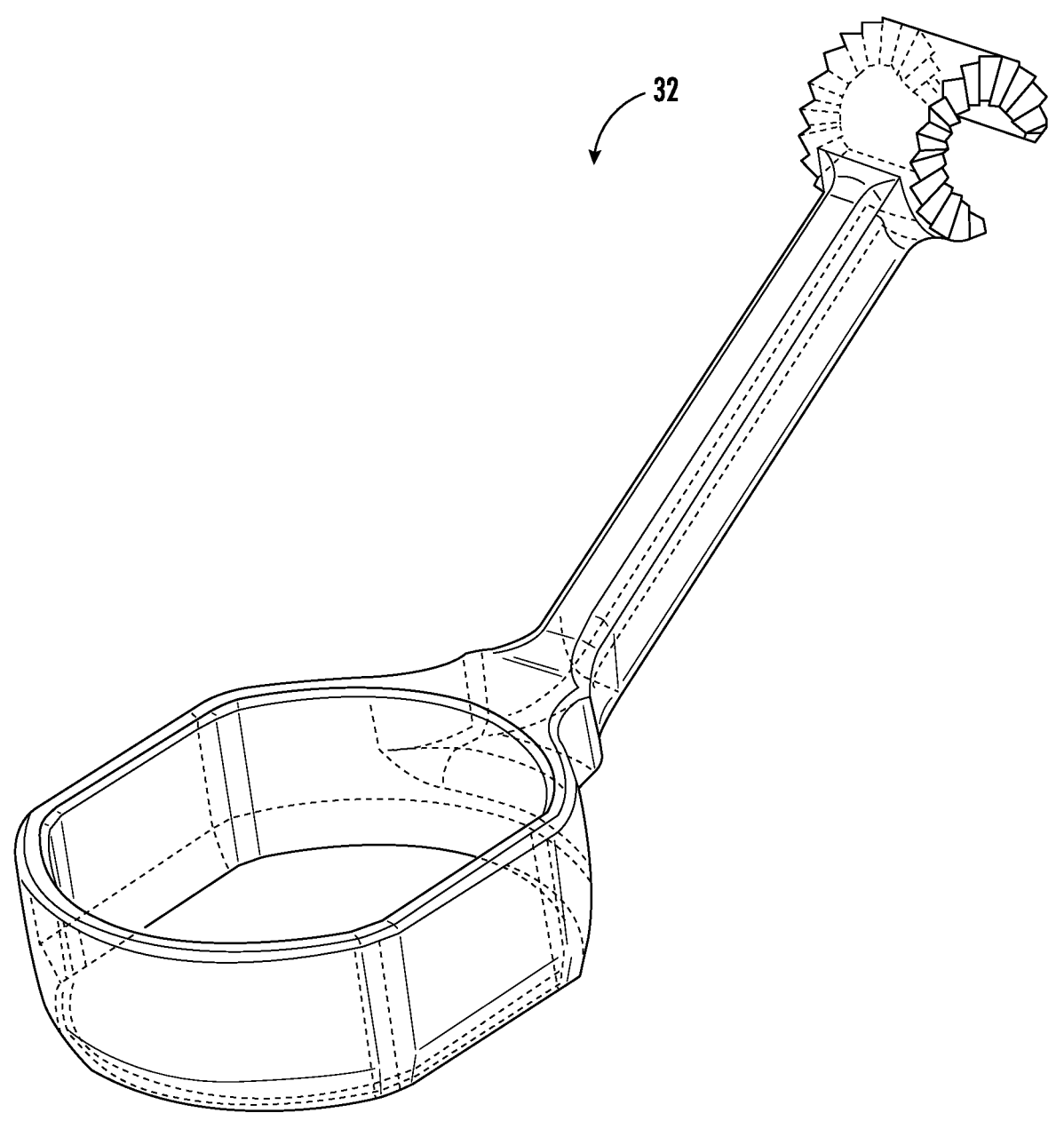
FIG. 2 depicts a view of a cannula arm in an embodiment of the invention

In an embodiment, the channel retractor 14 may include a cannula arm 32, as depicted in FIG. 2, for use to connect to a table mounted retractor arm. The cannula arm 32 and the table mounted retractor arm provide rigid fixation of the retractor 14 to the operating table in an embodiment.

Figure 5:
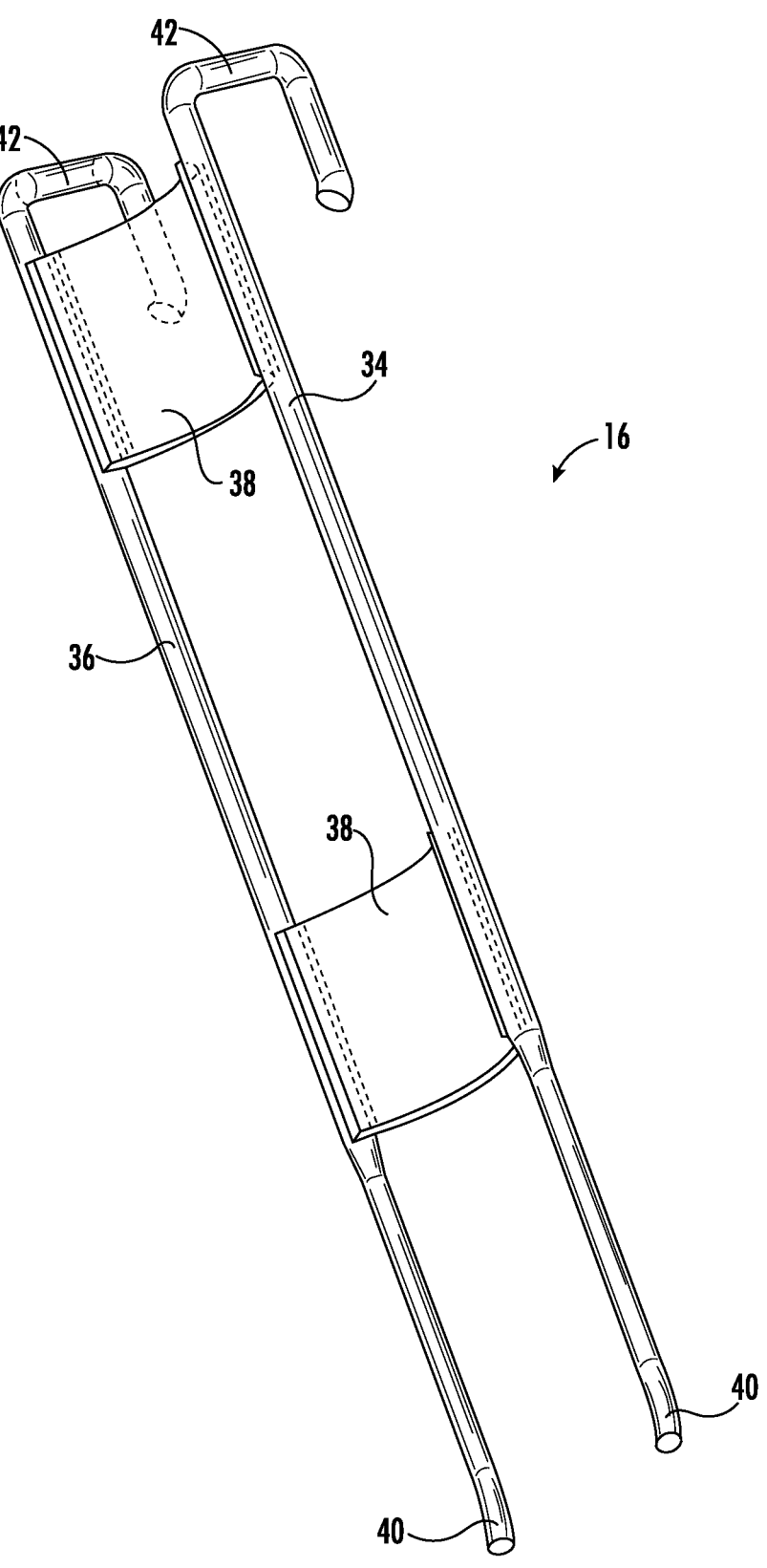
FIG. 5 depicts a spring clip in an embodiment of the invention.
Figure 6:
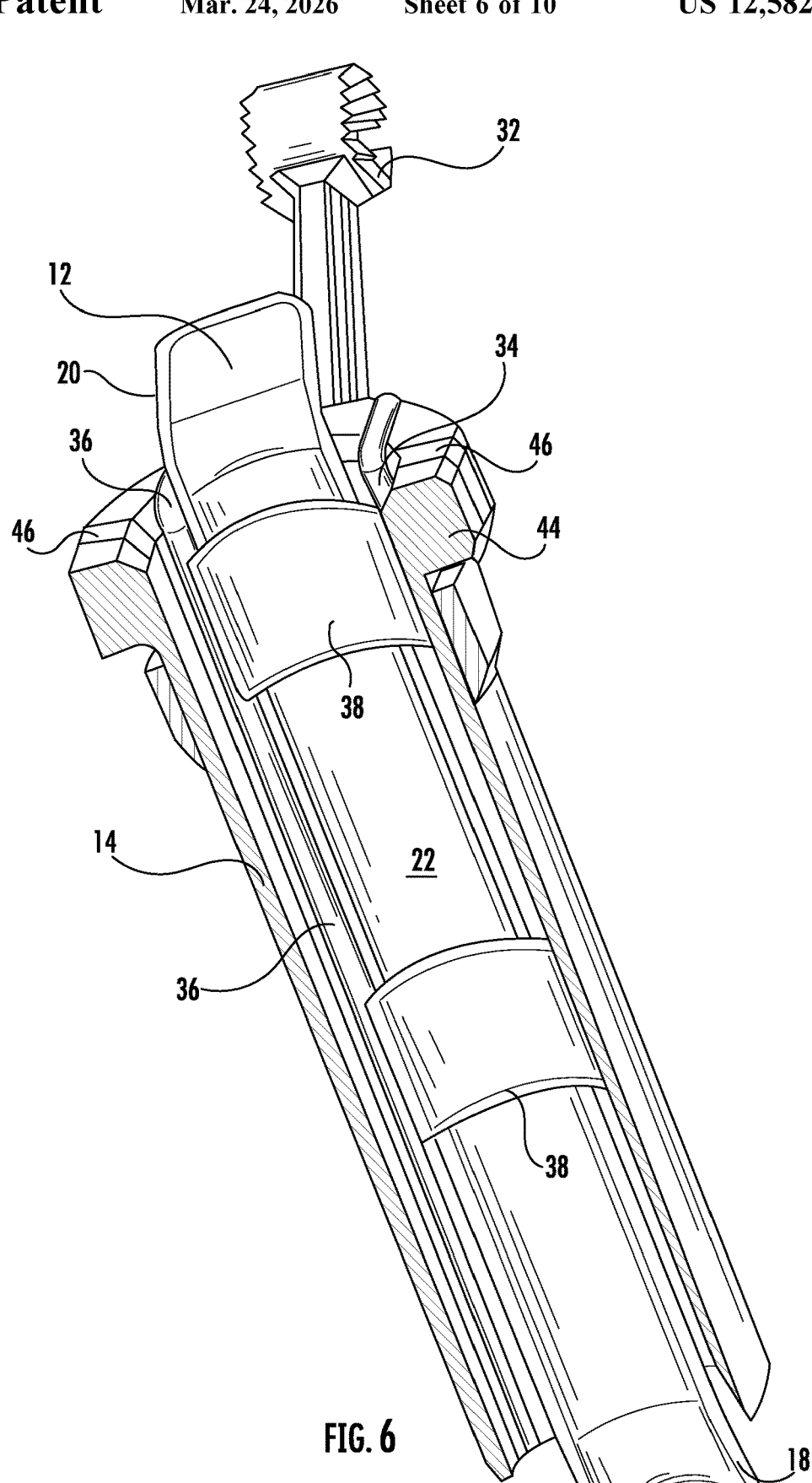
FIG. 6 depicts the location of attachment points in an embodiment of the invention.

The present inventor has recognized the need to solve the problem of a large moment and the resultant suboptimal forces placed upon the body or aspects of the retractor assembly 10 in an undesirable fashion. Embodiments of the invention, therefore, incorporate a spring clip 16, as depicted in FIG. 5. In an embodiment, a spring clip 16 attachably interacts with the proximal and distal end of one or more retractor blades 12 during the method of use of the invention, as depicted in FIG. 6. The spring clip 16 therefore functions to reduce the moment arm by securing near the distal end of the channel retractor 14. In the preferred embodiment, the one or more spring clips 16 secure the one or more retractor blades 12 to the channel retractor 14. The one or more spring clips 16 function to incorporate multiple attachment points for to facilitate a more secure connection to the channel retractor 14 in the preferred embodiment. In embodiments of the invention, the incorporation of one or more spring clips 16 allows at least one retractor blade 12 associated with an embodiment of the invention to be secured unilaterally. The present inventor has recognized that such configuration solves the problem associated with bi-lateral fixation associated with prior art solutions. Embodiments of the invention, as a result, therefore require only two hands to secure the retractor 14 during intended use instead of three.

Each spring clip 16 includes a first arm 34 and a second arm 36 that are connected by slat portions 38 that are sized and shaped to engage the body 22 of the retractor blades 12 and hold the retractor blades 12 in the desired position in the channel retractor 14. Each arm 34 and 36 includes distal ends 40 that engage with the distal holes 26 disposed on the inside of the channel retractor 14 and proximal ends 42 designed to securely engage with a lip 44 and/or edge of the channel retractor 14 proximally, as depicted in FIG. 1. In one embodiment, the proximal ends 42 of the arms 34 and 36 of the spring clip 16 can be formed to extend around the lip 44 of the channel retractor 14. The lip 44 can have recessed areas 46 to receive a portion of each arm 34 and 36 to prevent the spring clip 16 from moving around the internal circumference of the channel retractor 14.

An embodiment of the invention incorporates spring clip receptacles, such as distal holes 26, for attachment of the spring clip 16 near the distal end of the channel retractor 14. In such embodiment, one or more spring clips 16 slidably interact with the inner wall 24 of the channel retractor 14 to engage with the distal holes 26 comprising spring clip receptacles, as depicted in FIG. 7. More specifically, the distal ends 40 of the first and second arms 34 and 36 are extended into the distal holes 26 and the proximal ends 42 of the first and second arms 34 and 36 are forced around the lip 44 of the channel retractor 14.

Figure 8:
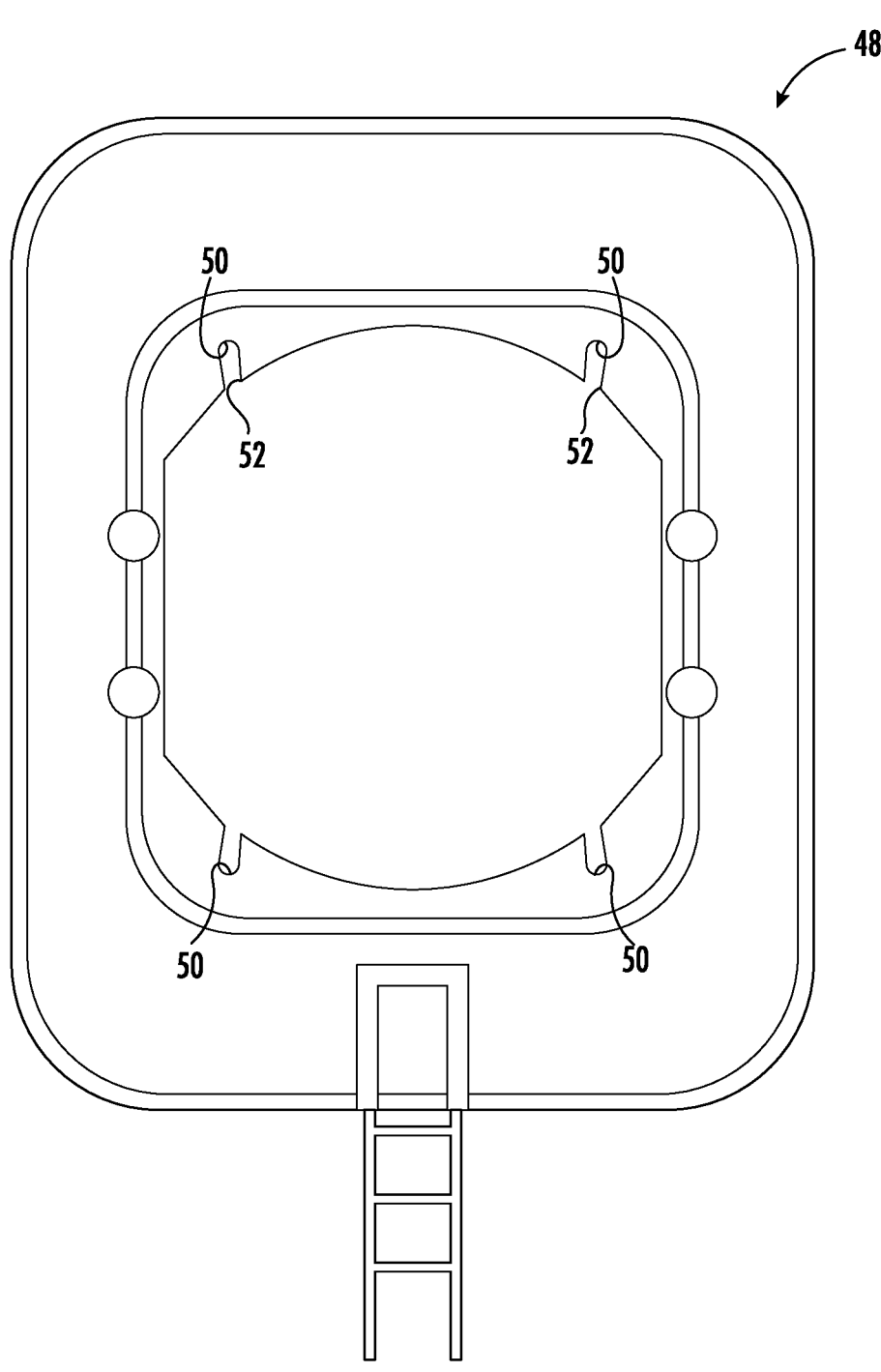
FIG. 8 depicts a view of ralingue features configured into an embodiment of the invention.

Ralingue. In another embodiment of the present disclosure, a Ralingue 48 refers to a slotted hole 50 with the slot opening 52 diameter smaller than the diameter of the hole 50. In other embodiments, the term Ralingue refers to the term Ralingue as commonly understood by those skilled in the art. In an embodiment, the channel retractor 14 incorporates one or more Ralingues 48 adjacent to and/or incorporated within the inner wall 24 of the channel retractor 14, as depicted in FIG. 8, configured to interact with a spring clip 16 configured as a Ralingue Clip as further defined herein. In one embodiment of the invention, the one or more Ralingues 48 are configured to be approximately 15 mm wide by 80 mm long, and 1.5 mm in depth.

Figures 9A, 9B:
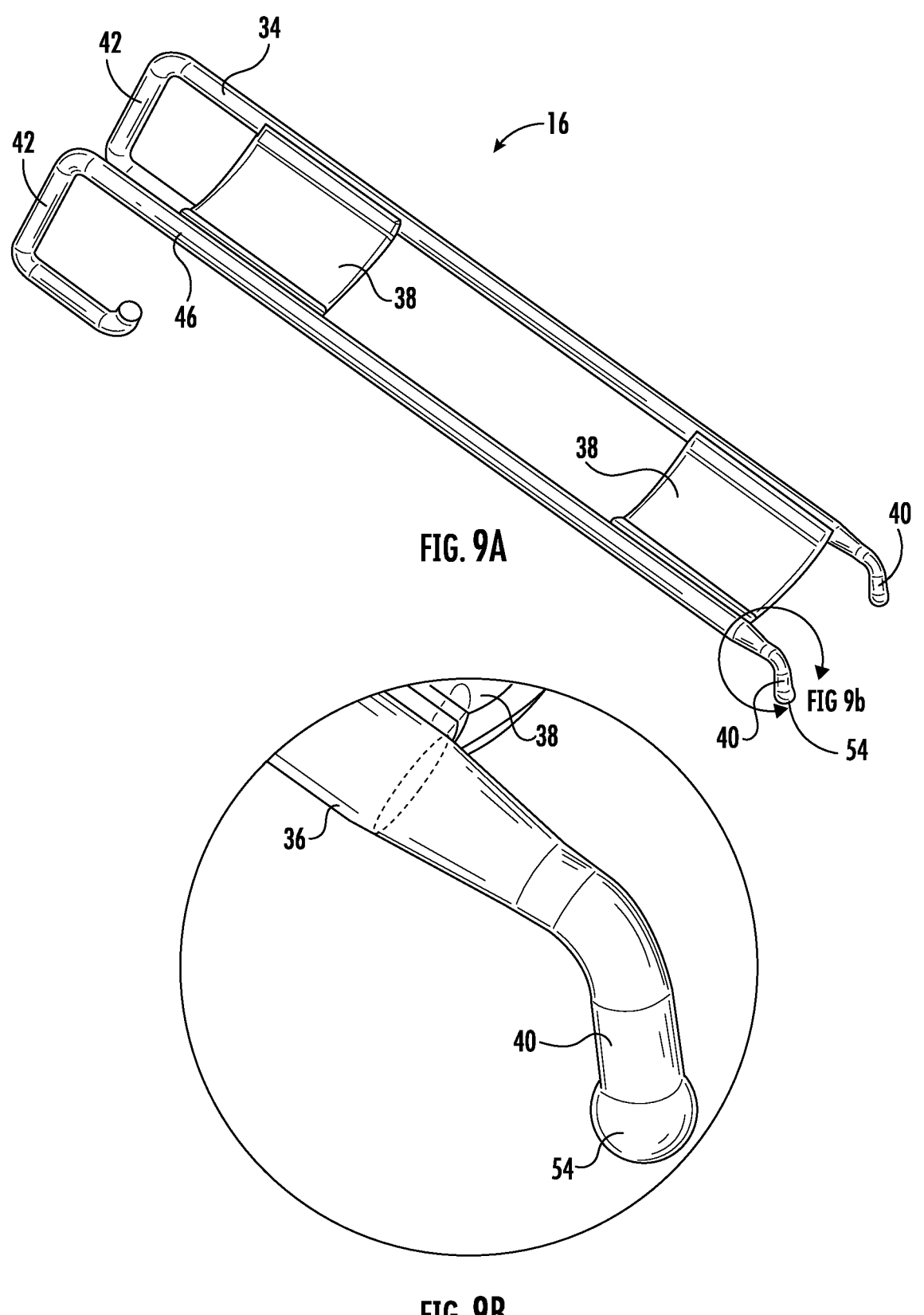
FIG. 9A depicts an embodiment of the spring clip configured with ralingue features in an embodiment of the invention.
FIG. 9B depicts an embodiment of the spring clip configured with ralingue features in an embodiment of the invention.
Figures 10A, 10B, 10C, 10D, 10E:
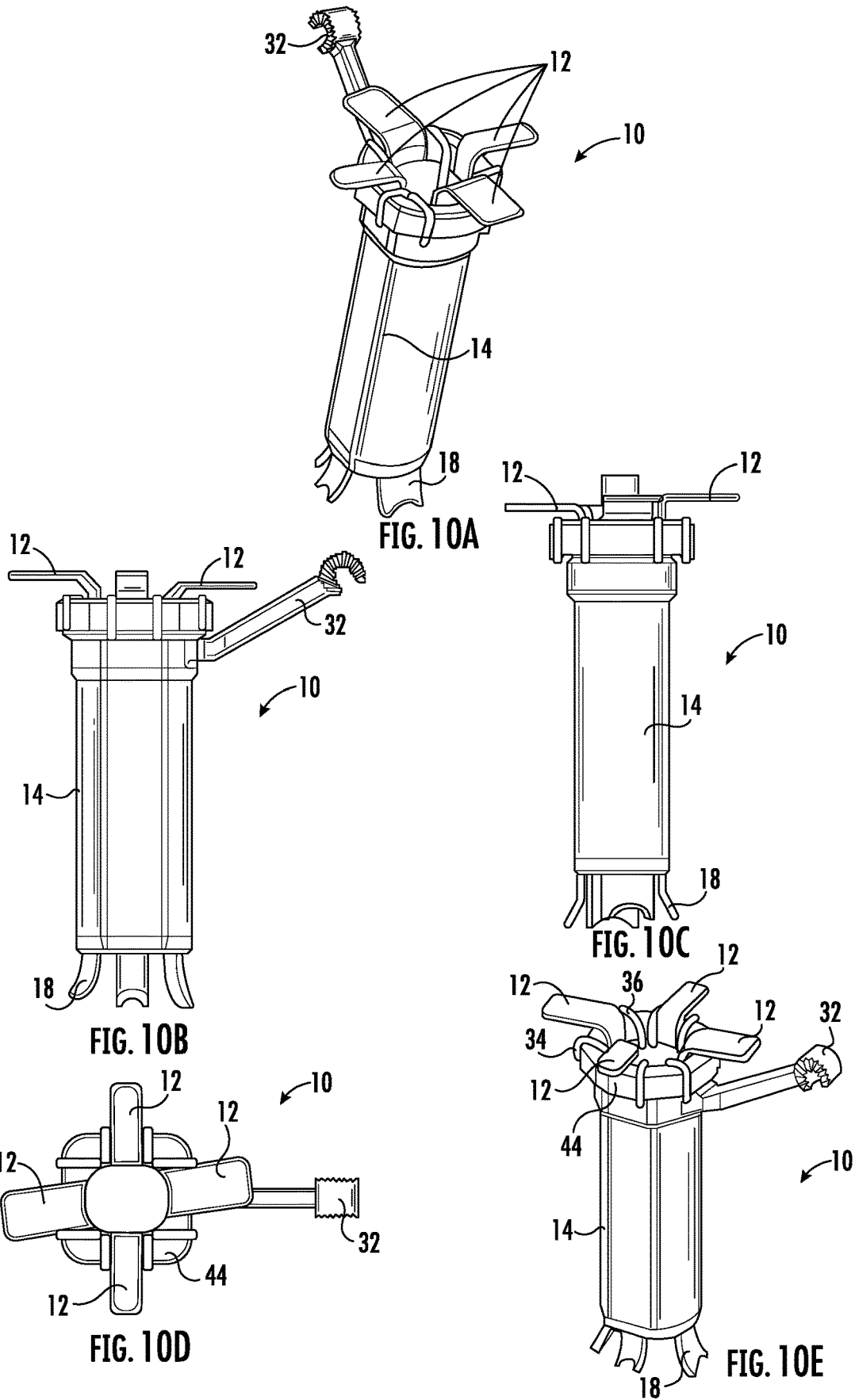
FIG. 10A depicts a view of a four-bladed retractor in an embodiment of the invention as assembled.
FIG. 10C depicts a view of a four-bladed retractor in an embodiment of the invention as assembled.
FIG. 10D depicts a view of a four-bladed retractor in an embodiment of the invention as assembled.
FIG. 10E depicts a view of a four-bladed retractor in an embodiment of the invention as assembled.

Ralingue Clip. In an embodiment of the invention, a spring clip 16 is configured as a "Ralingue Clip." In such embodiment, the distal ends 16 of the arms 34 and 36 of the spring clip 16 incorporates a ball feature 54, or fully radiused end, as depicted in FIG. 9. In such configuration, the distal ends 40 of the arms 34 and 36 of the spring clip 16, as depicted in FIG. 9b, interacts with the slotted hole of the Ralingue 48 such that the ball feature 54 of the spring clip 16 during the preferred method of use will slide into the slot of the Ralingue 48 incorporated into the channel retractor 14. In such embodiment, the spring clip 16 is retained in such a way that the ball features 54 will slide into the slotted hole 50 of the Ralingue clip but cannot exit the slotted hole 50 in any direction other than the direction substantially parallel to the slot axis.

In use, the retractor assembly 10 can be used by a single surgeon without assistance. Once an opening is created in the tissue, the retractor channel 14 of the retractor assembly 10 can be positioned in the tissue in close proximity to the surgical site to permit a doctor access to the surgical site. A retractor blade 12 can be extended through the channel retractor 14 to have the tissue end 18 of the retractor blade 12 engage tissue near a surgical site to position the tissue as desired by the doctor to provide better access to the surgical site. The spring clip 16 can then be extended down into the channel retractor 14 to engage various parts of the channel retractor 14 to maintain the position of the retractor blade 12 in the channel retractor 14. Additional retractor blades 12 can be extended into the channel retractor 14 and spring clips 16 can be extended into the channel retractor 14 to secure the additional retractor blades 12 in a desired position in the channel retractor 14.

One of skill in the art will recognize that the surgical procedures and related apparatuses set forth above may benefit from various kits of tools and components for use in these procedures. Kits may focus on reusable or disposable components for creating an access route. Other kits may focus on the tools for preparing the disc space. A kit may include many (possibly even all) the components necessary for a particular procedure including the components needed to create the access route, prepare the disc space and even the an assortment of implants. One of skill in the art will recognize that some of the alternative implementations set forth above are not universally mutually exclusive and that in some cases additional implementations can be created that employ aspects of two or more of the variations described above. Likewise, the present disclosure is not limited to the specific examples or particular embodiments provided to promote understanding of the various teachings of the present disclosure. Moreover, the scope of the claims which follow covers the range of variations, modifications, and substitutes for the components described herein as would be known to those of skill in the art. Individual claims may be tailored to claim particular embodiments out of the array of embodiments disclosed above. Some claims may be tailored to claim alternative embodiments rather than preferred embodiments. Some claims may cover an embodiment set forth above with a modification from another embodiment as the present disclosure does not include drawings of all possible combinations of feature sets.

What is claimed is:

1. A retractor assembly for providing customized access to a surgical site, the assembly comprising:

a channel retractor, the channel retractor includes distal holes disposed in the inner wall of a distal end;

a first retractor blade selectively positionable within the channel retractor, the first retractor blade having a tissue end for engaging desired tissue near the surgical site and a handle end for permitting a user to position the first retractor blade relative to the desired tissue and the channel retractor; and a spring clip to secure the first retractor blade to an inner wall of the channel retractor, the spring clip includes a first arm having a distal end and a proximal end and a second arm having a distal end and a proximal end, the first and second arm are attached by at least one plate portion, the distal ends of the first and second arms sized to fit in the distal holes of the channel retractor and the proximal ends of the first and second arm designed to engage a lip of the channel retractor, the plate portion is designed to engage the retractor blade against the inner wall of the channel retractor.

2. The assembly of claim 1 wherein the channel retractor includes a lip on a proximal end of the channel retractor.

3. The assembly of claim 2 wherein the channel retractor includes slotted holes with openings disposed in the inner wall of the channel retractor wherein the openings have a diameter that is smaller than the diameter of the slotted holes.

4. The assembly of claim 3 wherein the spring clip includes a first arm having a distal end and a proximal end and a second arm having a distal end and a proximal end, the first and second arm are attached by at least one plate portion, the distal ends of the first and second arms include ball elements sized to fit in the slotted holes of the channel retractor and the proximal ends of the first and second arm designed to engage the lip of the channel retractor, the plate portion is designed to engage the retractor blade against the inner wall of the channel retractor.

5. The assembly of claim 1 wherein the channel retractor includes a first recessed area disposed on the inner wall for receiving the first arm of the spring clip and a second recessed area disposed on the inner wall for receiving the second arm of the spring clip to help restrict movement of the spring clip in the channel retractor.

6. The assembly of claim 5 wherein the first and second recessed areas extend around a portion of the lip of the channel retractor.

7. The assembly of claim 1 wherein the retractor assembly includes four retractor blades and four spring clips.

8. The assembly of claim 1 wherein the retractor assembly includes a cannula arm to secure the retractor assembly in a desired location.

\* \* \* \* \*